: US 7,718,631 B2

United States Patent
Chen et al.

(10) Patent No.: US 7,718,631 B2
(45) Date of Patent: May 18, 2010

(54) TREATMENT TOOL FOR CANCER: RNA INTERFERENCE OF BCAS2

(75) Inventors: Show-Li Chen, Taipei (TW); Shinn-Tsuen Lin, Yilan County (TW); Hung-Wei Chang, Taipei County (TW)

(73) Assignee: National Taiwan University, Taipei (TW)

( * ) Notice: Subject to any disclaimer, the term of this patent is extended or adjusted under 35 U.S.C. 154(b) by 118 days.

(21) Appl. No.: 12/062,478

(22) Filed: Apr. 3, 2008

(65) Prior Publication Data
US 2008/0221059 A1 Sep. 11, 2008

(51) Int. Cl.
*A61K 31/70* (2006.01)
*C07H 21/02* (2006.01)
*C07H 21/04* (2006.01)
*C12N 5/00* (2006.01)
*C12Q 1/68* (2006.01)

(52) U.S. Cl. .................. 514/44; 536/23.1; 536/24.1; 536/24.5; 435/6; 435/375; 435/377; 435/320.1

(58) Field of Classification Search ............... None
See application file for complete search history.

(56) References Cited

U.S. PATENT DOCUMENTS

2004/0259247 A1* 12/2004 Tuschl et al. ............... 435/375
2005/0255487 A1* 11/2005 Khvorova et al. ............ 435/6
2007/0009899 A1* 1/2007 Mounts ..................... 435/6

OTHER PUBLICATIONS

Brummelkamp et al., Science vol. 296:550-553, 2002.*
Worsham et al., Breast Cancer Research and Treatment vol. 96:177-186, 2006.*
Qi et al., Biocemical and Biophysical Research Communications vol. 328:393-398, 2005.*
Nicolai Maass et al.; Amplification of the BCAS2 gene at chromosome 1p13/3-21 in human primary breast cancer; Journal; 2002; pp. 219-223; vol. 185; Cancer Letters; Elsevier Science Ireland Ltd.
Gitte Neubauer et al.; Mass spectrometry and EST-database searching allows characterization of the multi-protein spliceosome complex; Journal; Sep. 1998; pp. 46-50; vol. 20; Letter; Nature Genetics; Nature America Inc.

* cited by examiner

*Primary Examiner*—Sean R McGarry
(74) *Attorney, Agent, or Firm*—WPAT, P.C.; Anthony King (57) ABSTRACT

The present invention provides three BCAS2 related nucleotide sequences. The present invention also provides a composition comprising a nucleotide sequence of small interfering RNA of BCAS2 gene. The present invention further provides a method for treating p53 containing cancer comprising administrating a subject with an effective amount of the said composition.

9 Claims, 12 Drawing Sheets

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: synthesized sequence corresponds to BCAS2
      position 331-349
<220> FEATURE:
<221> NAME/KEY: misc_feature
<222> LOCATION: (1)..(19)

<400> SEQUENCE: 1
tggcccagtt agagcatca                                                  19

<210> SEQ ID NO 2
<211> LENGTH: 19
<212> TYPE: DNA
<213> ORGANISM: Artificial
<220> FEATURE:
```

```
<223> OTHER INFORMATION: synthesized sequence corresponding to BCAS2
      position 434-452
<220> FEATURE:
<221> NAME/KEY: misc_feature
<222> LOCATION: (1)..(19)

<400> SEQUENCE: 2
gattgaacac gcacagaag                                                      19

<210> SEQ ID NO 3
<211> LENGTH: 19
<212> TYPE: DNA
<213> ORGANISM: Artificial
<220> FEATURE:
<223> OTHER INFORMATION: synthesized sequence corresponding to BCAS2
      position 510-528
<220> FEATURE:
<221> NAME/KEY: misc_feature
<222> LOCATION: (1)..(19)

<400> SEQUENCE: 3
caactcacag ctggatcta                                                      19

<210> SEQ ID NO 4
<211> LENGTH: 21
<212> TYPE: DNA
<213> ORGANISM: Artificial
<220> FEATURE:
<223> OTHER INFORMATION: synthesized sequence corresponding to BCAS2
      position 135-155
<220> FEATURE:
<221> NAME/KEY: misc_feature
<222> LOCATION: (1)..(21)

<400> SEQUENCE: 4
ggaagcggct gcagcgctgg t                                                   21
```

TREATMENT TOOL FOR CANCER: RNA INTERFERENCE OF BCAS2

FIELD OF THE INVENTION

The present invention relates to three BCAS2 related nucleotide sequences. The present invention also relates to a composition comprising a nucleotide sequence of small interfering RNA of BCAS2 gene. The present invention further relates to a method for treating p53 containing cancer comprising administrating a subject with an effective amount of the said composition.

BACKGROUND

RNA interference (also called "RNA-mediated interference", abbreviated RNAi) is a mechanism for RNA-guided regulation of gene expression in which double-stranded ribonucleic acid inhibits the expression of genes with complementary nucleotide sequences. Conserved in most eukaryotic organisms, the RNAi pathway is thought to have evolved as a form of innate immunity against viruses and also plays a major role in regulating development and genome maintenance.

The RNAi pathway is initiated by the enzyme dicer, which cleaves double-stranded RNA (dsRNA) to short double-stranded fragments of 20-25 base pairs. One of the two strands of each fragment, known as the guide strand, is then incorporated into the RNA-induced silencing complex (RISC) and base-pairs with complementary sequences. The most well-studied outcome of this recognition event is a form of post-transcriptional gene silencing. This occurs when the guide strand base pairs with a messenger RNA (mRNA) molecule and induces degradation of the mRNA by argonaute, the catalytic component of the RISC complex. The short RNA fragments are known as small interfering RNA (siRNA) which are perfectly complementary to the gene to which they are suppressing as they are derived from long dsRNA of that same gene or MicroRNA (miRNA) which are derived from the intragenic regions or an intron and are thus only partially complementary. The RNAi pathway has been particularly well-studied in certain model organisms such as the nematode worm *Caenorhabditis elegans*, the fruit fly *Drosophila melanogaster*, and the flowering plant *Arabidopsis thaliana*.

The selective and robust effect of RNAi on gene expression makes it a valuable research tool, both in cell culture and in living organisms; synthetic dsRNA introduced into cells can induce suppression of specific genes of interest. RNAi may also be used for large-scale screens that systematically shut down each gene in the cell, which can help identify the components necessary for a particular cellular process or an event such as cell division. Exploitation of the pathway is also a promising tool in biotechnology and medicine.

However, applying RNAi via siRNAs to living animals, especially humans, poses many challenges. siRNAs show different effectiveness in different cell types in a manner yet poorly understood: some cells respond well to siRNAs and show a robust knockdown, others show no such knockdown (even despite efficient transfection).

BCAS2 (Breast carcinoma amplified sequence 2) is a gene isolated from breast cancer cell line by differential display technique. (Nagasaki K et al [*Amplification of the BCAS2 Gene at Chromosome* 1p13.3-21 in *Human Primary Breast Cancer*, Cancer Lett. 1999 Jun. 1; 140(1-2):219-26]) This family consists of several eukaryotic sequences of unknown function. The mammalian members of this family are annotated as breast carcinoma amplified sequence 2 (BCAS2) proteins. (Neubauer G, King A, Rappsilber J, Calvio C, Watson M, Ajuh P, Sleeman J, Lamond A, Mann M; Nat Genet. 1998; 20:46-50: Mass spectrometry and EST-database searching allows characterization of the multi-protein spliceosome complex.) BCAS2 is a putative spliceosome associated protein. (Neubauer G, King A, Rappsilber J, Calvio C, Watson M, Ajuh P, Sleeman J, Lamond A, Mann M; Nat Genet. 1998; 20:46-50: Mass spectrometry and EST-database searching allows characterization of the multi-protein spliceosome complex.)

p53, also known as protein 53 (TP53), is a transcription factor that regulates the cell cycle and hence functions as a tumor suppressor. It is important in multicellular organisms as it helps to suppress cancer. p53 has been described as "the guardian of the genome", "the guardian angel gene", or the "master watchman", referring to its role in conserving stability by preventing genome mutation.

SUMMARY OF THE INVENTION

The present invention provides three BCAS2 related nucleotide sequences. The present invention also provides a composition comprising a nucleotide sequence of small interfering RNA of BCAS2 gene. The present invention further provides a method for treating p53 containing cancer comprising administrating a subject with an effective amount of the said composition.

DETAILED DESCRIPTION OF THE INVENTION

BCAS2 was isolated using the androgen receptor as the bait to screen a human Hela MATCHMAKER cDNA library in a yeast-two hybrid screening. Full length sequence of BCAS2 cDNA is the same as DAM1 (*Mus musculus* DNA amplified in mammary carcinoma mRNA) reported on July, 2001 at NCBI. It contained a full coding region of 678 bp encoding 225 amino acids with the predicted molecular mass of 26 kDa and expressed in nucleus. BCAS2 is an ubiquitous gene and its conservative evolution might have an important biological role in mammalian cell.

RNA interference (RNAi) had been proven to be a powerful tool to silence gene expression in a sequence specific manner. Recent advances in the understanding of RNAi had provided practical tools to knock down gene expression in mammalian cells, thus made it possible to generate gene knock-out models for investigating the functions of BCAS2 genes on nuclear reporter transactivation. In the present invention, the pSUPER vector-based siRNA system was used for demonstration. Short sequences of the various siRNAs were designed to correspond to the BCAS2 nucleotide position, named siBCAS2. RNAi clones were introduced into MCF-7 cells (Human breast adenocarcinoma cell line) and analyzed by anti-BCAS2 antibody. BCAS2 protein expression is affected by the addition of siBCAS2. The designed sequence of siBCAS2 targets to the BCAS2 mRNA and diminishes the expression of BCAS2. On the other hand, the cell growth rate is measured in siBCAS2-transfected cancer cell lines. The result shows that siBCAS2 reduces cancer cell growth and increases cancer cell death ratio.

The mechanism of siBCAS2-inhibiting growth is determined by measuring p21 WAF1/CIPI (p21) and BCAS2 protein expression under the introduction of siBCAS2 into cells. The p21 protein is increased and correlated with the declined expression of BCAS2. The p21 gene was reported to be p53 target genes which contained a p53 responsive element to be activated by p53. Thus, the role of BCAS2 in p53 protein function is examined in the present invention. GST-BCAS2 pull down assay is conducted and the result presents that the p53 binds BCAS2. The co-immunoprecipitation assay is performed to measure the protein-protein interaction between p53 and BCAS2 in p53 containing cancer cells. In sum, BCAS2 can bind to p53 and siBCAS2 treatment causes the relief p53 from the bounded BCAS2 and allows p53 to induce p21 gene expression.

To confirm that BCAS2 is a negative regulator of p53, p21 gene expression under p53 induction was investigated by introducing various does of BCAS2-expression plasmid into cancer cells. The result shows that p21 promoter activity decreases proportionally as the amount of BCAS2 increased, this indicates that BCAS2 is an inhibitor of p53. The bounded p53 by BCAS2 would cause p53 inactive, but as siBCAS2 is introduced into the cancer cell, it silences the BCAS2 gene expression, therefore p53 is freed and available to trigger p21 promoter activity. The result shows that the gene expression of p21 is proportional to the dosage of siBCAS2.

The present invention provides a promising tool in treating cancers that contain p53. It is known that p53 which acts as a transcriptional regulatory factor in cell cycle can function as a tumor suppressor. Since BCAS2, the gene product appears in various cancer cells, is showed to bind p53 and inactivate p53; BCAS2 is a good target for cancer therapy. The siRNA clones for BCAS2 provided in the present invention can be applied to shut down BCAS2 expression and recover the function of p53 in triggering p21 expression. The p21 mediates apoptosis of cancer cells and thus reduces cancer cell growth.

Accordingly, the present invention provides nucleotide sequences of SEQ ID NO:1, SEQ ID NO:2 and SEQ ID NO:3. They are siRNA sequences of BCAS2 gene in the present invention.

The present invention also provides a composition comprising a nucleotide sequence of small interfering RNA of BCAS2 gene.

In preferred embodiments, the nucleotide sequence in the said composition is SEQ ID NO: 1, SEQ ID NO: 2 or SEQ ID NO: 3.

In the most preferred embodiment, the nucleotide sequence in the said composition is SEQ ID NO: 2.

In one embodiment, the nucleotide sequence is constructed in a RNAi vector. In a preferred embodiment, the RNAi vector is pSuper.

The present invention also provides a method for treating p53 containing cancer (such as breast cancer, prostate cancer or lung cancer), comprising administrating a subject with an effective amount of the said composition.

In a preferred embodiment, the p53 containing cancer is breast cancer.

In one embodiment, the subject is a mammal. In a preferred embodiment, the subject is a mouse. In a more preferred embodiment, the subject is a human.

EXAMPLES

The examples below are non-limiting and are merely representative of various aspects and features of the present invention.

Example 1

The Interaction of BCAS2 and p53

Figure 1:
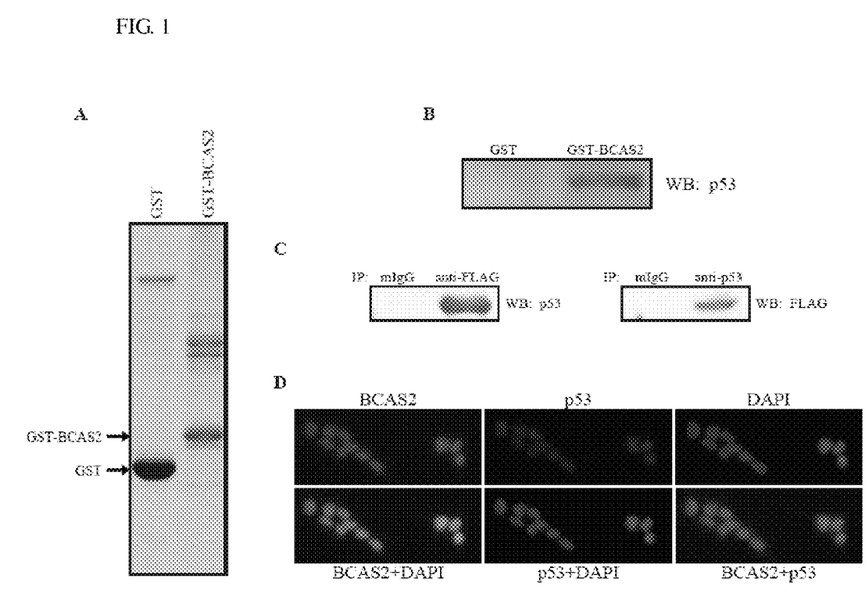
FIG. 1 shows (A) SDS-PAGE of proteins interacting with BCAS2. GST was used as a negative control; (B) western blot analysis of GST and GST-BCAS2 using anti-p53 as antibody; (C) western blot analysis of immunoprecipitation products of anti-FLAG (left) or anti-p53 (right) using anti-p53 (left) or anti-FLAG (right) as antibody; (D) immuno-fluorescence staining of BCAS2 and p53.

The full-length of BCAS2 cDNA were cloned to pGEX-4T-1 vector to generate GST fusion proteins, named pGEX-4T1-BCAS2, wherein GST was tagged at 5'-end of the BCAS2 gene. Expression of the fusion proteins was induced by 0.1 mM IPTG for 3 h, and the fusion proteins present in the inclusion bodies were solubilized by denaturation with 6 M urea. The fusion proteins were allowed to refold by dialysis to remove urea and then purified by incubating with glutathione-Sepharose 4B beads. The beads were washed five times with wash buffer containing 10 mM Tris-HCl (pH 8.0), 120 mM NaCl, 1 mM EDTA, and 0.1% NP-40, and the fusion proteins were eluted by elution buffer containing 50 mM Tris-HCl (pH 8.0) and 5 mM reduced glutathione. For pull-down analysis, equal amounts of GST fusion proteins immobilized on beads were incubated with MCF-7 cell nuclear lysates. The beads were washed, and proteins bound on beads were analyzed by SDS-PAGE (FIG. 1A), Western blot analysis or Mass spectrometry.

Anti-p53 antibody (DO1; Santa Cruz) was used for Western blot analysis. The result showed that p53 interacted with BCAS2 instead of GST (FIG. 1B). To confirm the result, the plasmid was transfected into MCF-7 cell for FLAG-BCAS2 expression. MCF-7 cell was maintained in RPMI 1640 medium supplemented with 10% fetal bovine serum and antibiotics. Prior to transfection, cells were washed with FBS free media, then trypsinization. Washing cells by antibiotics-free media with 2.5% FBS twice, then suspend cells almost $1\times10^7$ cells/ml. The Electroporation Procedure was modified by standard procedures provide by BTX. Anti-FLAG (M2; Sigma) or anti-p53 antibody was used. The cell lysates from cells transfected with expression plasmids or control vector were subjected to immunoprecipitation with antibodies against either p53 or FLAG-epitope. The bound proteins were separated on 12.5% SDS-PAGE, blotted with specific antibody, and detected using an ECL Western blotting detection system (Amersham Biosciences). The photograph images were captured by UVP BioSpectrumAC Imaging System. The result demonstrated that BCAS2 interacted with p53 (FIG. 1C).

Human 293T cells were transfected with pEGFP-C1-BCAS2 by calcium-phosphate method. 293T cells were maintained in Dulbecco's modified Eagle's medium supplemented with 10% fetal bovine serum and 1% minimal essential medium non-essential amino acids solution. The expression vector pEGFP-C1 vector was generated by tagging EGFP at 5'-end of the BCAS2 gene, then named pEGFP-C1-BCAS2. Forty-eight hours after transfection, cells were fixed with 4% paraformaldehyde and stained with 0.2 μg/ml DAPI (4,6-diamidino-2-phenylindole dihydrochloride, blue color; Sigma). Fluorescent GFP-BCAS2 was monitored by a Leica fluorescence microscope. MCF-7 cells were fixed by PBS with 4% paraformadehyde. Cells were double stained with an anti-p53 or anti-BCAS2, followed by incubation with FITC-conjugated anti-rabbit and Alexa Fluor-conjugated anti-mouse atibodies. Nucleus signal was stain with DAPI. Fluorescent images were monitored by an Olympus fluorescence microscope. The result showed that BCAS2 and p53 co-localized in cell nucleus (FIG. 1D).

Example 2

Design and Construction of siRNA

Figure 2:
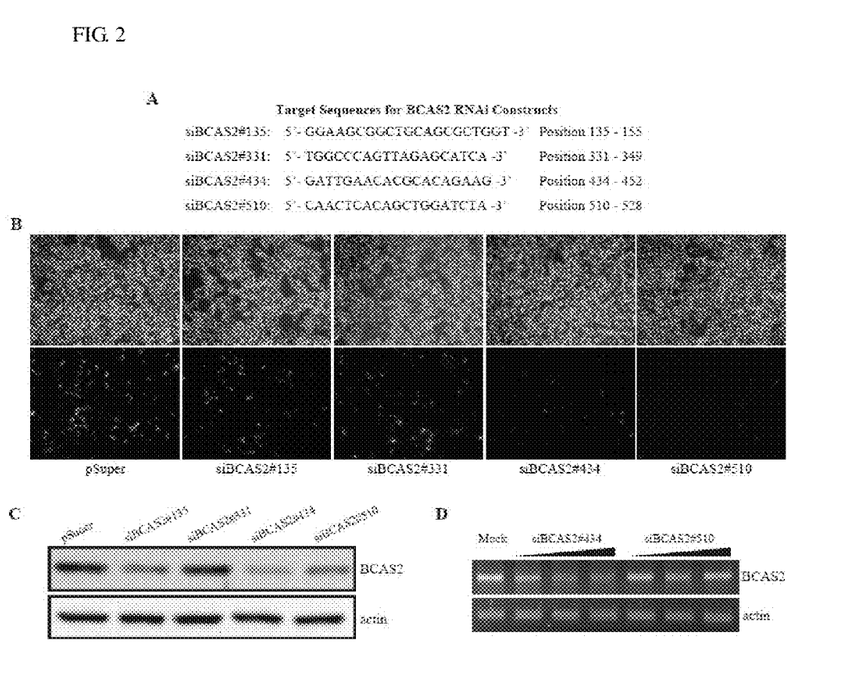
FIG. 2 shows (A) target sequences for BCAS2 RNAi constructs; (B) the intensity of fluorescence in cells transfected with EGFP-BCAS2 and various BCAS2 RNAi constructs; (C) western blot analysis of MCF-7 cells transfected with various BCAS2 RNAi constructs using anti-BCAS2 as antibody; (D) estimation of BCAS2 mRNA expression in siBCAS2#434 and siBCAS2#510 transfected 293T cells by RT-PCR. pSuper: vector only (control), Mock: electroporation without plasmid.

The pSuper vector-based RNAi system was used in the present invention. Based on empirical guidelines, four 19- or 20-nucleotide stretches within the coding region of BCAS2 were designed, ~50% GC-rich and unique in the human genome. Accordingly, three siBCAS2 nucleotide sequences were synthesized as shown in SEQ ID NO: 1, SEQ ID NO: 2 and SEQ ID NO: 3 (FIG. 2A). The gene-specific targeting sequence was subsequently subcloned downstream of the H1-RNA promoter between the BglII and HindIII sites in a pSuper vector. The siBCAS2#331 (containing SEQ ID NO: 1), siBCAS2#434 (containing SEQ ID NO: 2), and siBCAS2#510 (containing SEQ ID NO: 3) were constructed.

Example 3

RNAi Effect of siBCAS2

The EGFP-BCAS2 vector was co-transfected with pSuper and various RNAi clones of siBCAS2 [siBCAS2#135 (SEQ ID NO: 4), siBCAS2#331, siBCAS2#434, and siBCAS2#510] respectively into 293T cells. 293T cells were maintained in Dulbecco's modified Eagle's medium supplemented with 10% fetal bovine serum and 1% minimal essential medium non-essential amino acids solution. The RNAi effect was estimated by observing the fluorescence expression. The result shown that siBCAS2#434 and siBCAS2#510 had better RNAi effect than siBCAS2#135 and siBCAS2#331 (FIG. 2B). In order to determine the knock-down ability of these siBCAS2, the various RNAi clones of siBCAS2 (siBCAS2#135, siBCAS2#331, siBCAS2#434, and siBCAS2#510) were transfected into MCF-7 cells (maintained as described above) and analyzed by Western blot analysis. Actin was used as internal control. Anti-actin were from Sigma. BCAS2 expression was measured using anti-BCAS2 antibodies (Bethyl Laboratories, USA). The result shown that siBCAS2#135, siBCAS2#434 and siBCAS2#510 could silence BCAS2 well. (FIG. 2C)

The RNAi clones of siBCAS2#434 and siBCAS2#510 with various concentrations were further transfected into 293T cells (maintained as described above). The BCAS2 mRNA expressions of the transfected cells were measured by RT-PCR. The result shown that the RNAi effect of siBCAS2#434 was dose-dependent (FIG. 2D).

Example 4

The Effect of siBCAS2 on Cancer Cell Growth

The RNAi clone of siBCAS2#434 was transfected into MCF-7 cell (Human breast adenocarcinoma cell line) and LNCaP cell (human prostate adenocarcinoma cell line). MCF-7, LNCaP, and H1299 cells were maintained in RPMI 1640 medium supplemented with 10% fetal bovine serum and antibiotics. Prior to transfection, cells were washed with FBS free media, then trypsinization. Washing cells by antibiotics-free media with 2.5% FBS twice, then suspend cells almost $1\times10^7$ cells/ml. The Electroporation Procedure was modified by standard procedures provide by BTX.

Figure 3:
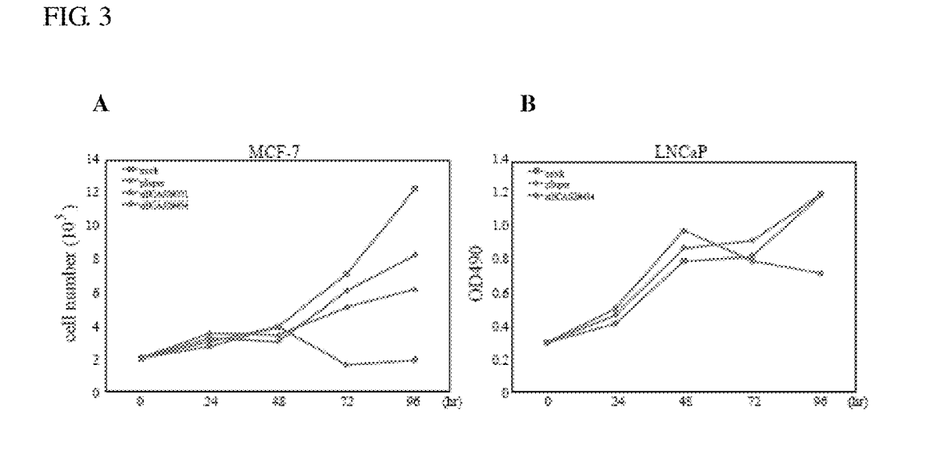
FIG. 3 shows cell number/$OD_{490}$ of (A) MCF-7 cell and (B) LNCaP cell transfected with siBCAS2.

The growth curves of the transfected cells were observed. The result showed that siBCAS2#434 retarded cancer cell growth (FIG. 3).

Example 5

The Effect of siBCAS2 on Cancer Cell Death

Figure 4:
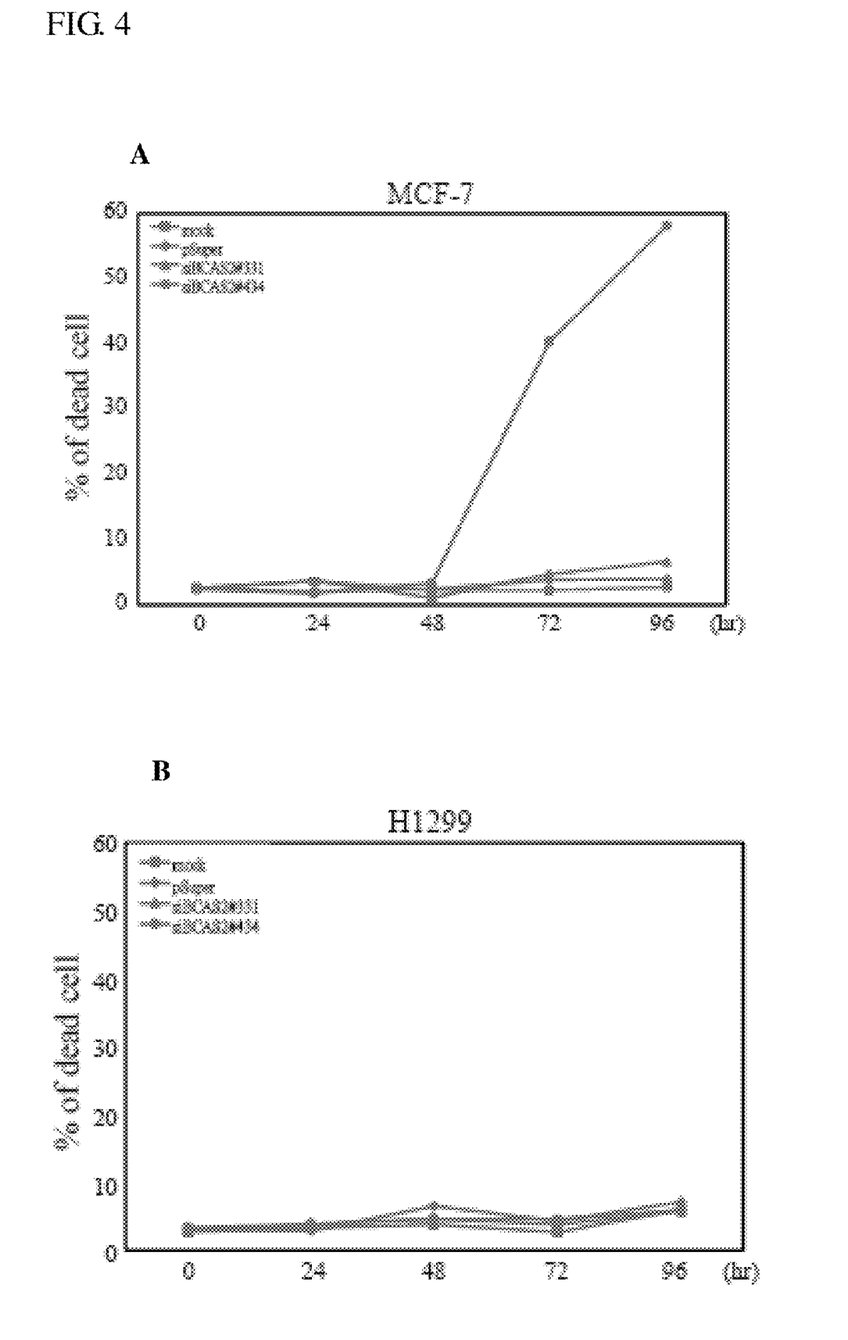
FIG. 4 shows percentages of dead cells in (A) MCF-7 cell and (B) H1299 cell transfected with siBCAS2.

The RNAi clone of siBCAS2#434 was transfected into MCF-7 cell and H1299 cell (lung cancer cell line). MCF-7 cell was maintained as described above and H1299 cells were maintained in RPMI 1640 medium supplemented with 10% fetal bovine serum and antibiotics. Prior to transfection, cells were washed with FBS free media, then trypsinization. Washing cells by antibiotics-free media with 2.5% FBS twice, then suspend cells almost $1\times10^7$ cells/ml. The Electroporation Procedure was modified by standard procedures provide by BTX. Both of the living and dead transfected cells H1299 cells were maintained in RPMI 1640 medium supplemented with 10% fetal bovine serum and antibiotics. Prior to transfection, cells were washed with FBS free media, then trypsinization. Washing cells by antibiotics-free media with 2.5% FBS twice, then suspend cells almost $1\times10^7$ cells/ml. The Electroporation Procedure was modified by standard procedures provide by BTX. The transfected cells were stained by trypan blue. Living and dead cells were then counted. The result shown that siBCAS2#434 increased the death of p53 containing MCF-7 cell but did not affect p53 null H1299 cell (FIG. 4).

Example 6

The Effect of siBCAS2 on Cancer Cell Foci Formation

Figure 5:
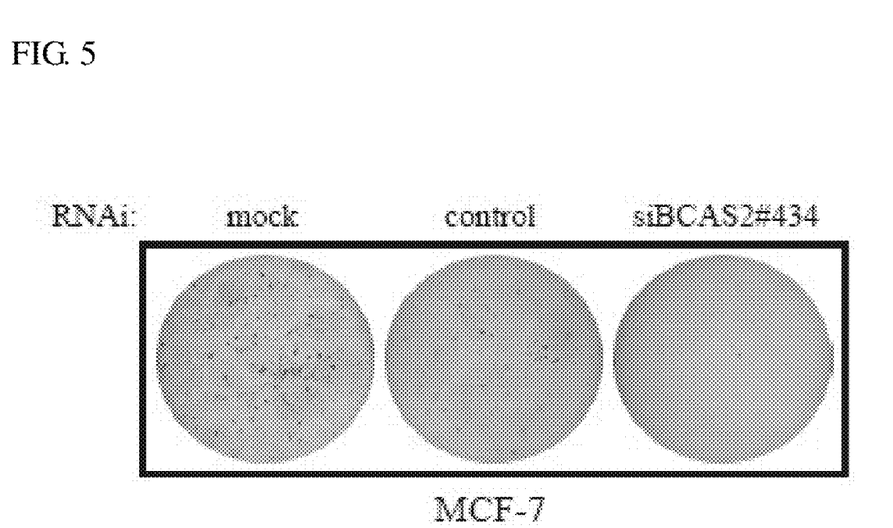
FIG. 5 shows the result of colony formation assay of MCF-7 cells transfected with siBCAS2#434. pSuper: vector only (control), Mock: electroporation without plasmid.

The RNAi clone of siBCAS2#434 and pSuper vector only was transfected into MCF-7 cell as described above. pSuper was used as control. The result of colony formation assay of the transfected cells and the cell executed Electroporation Procedure without introducing any plasmid (mock) shown that silence of BCAS2 by siBCAS2#434 reduced foci formation of MCF-7 cells (FIG. 5).

Example 7

The Effect of siBCAS2 on p53 Down-Stream Gene

Figure 6:
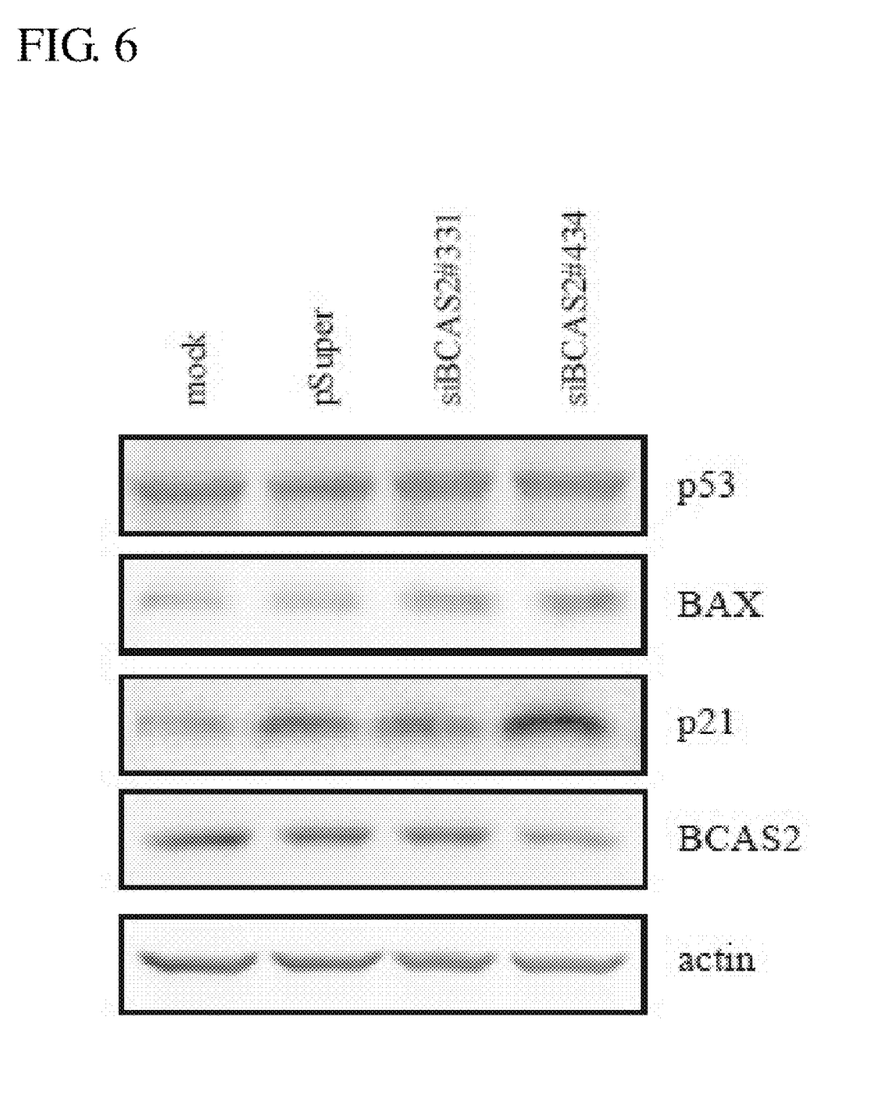
FIG. 6 shows the expression of p53, BAX, p21 and BCAS2 in cells transfected with siBCAS2. The actin is used as internal control.

Western blot analysis was taken to estimate the expression of p21 and BAX in siBCAS2 containing cells. Both of p21 and BAX were p53 down-stream genes and mediated apoptosis. Anti-p21 antibody was from Cell Signalling, and anti-BAX antibody was from Upstate. The result showed that silence of BCAS2 by siBCAS2 increased the expression of p21 and BAX (FIG. 6).

Figure 7:
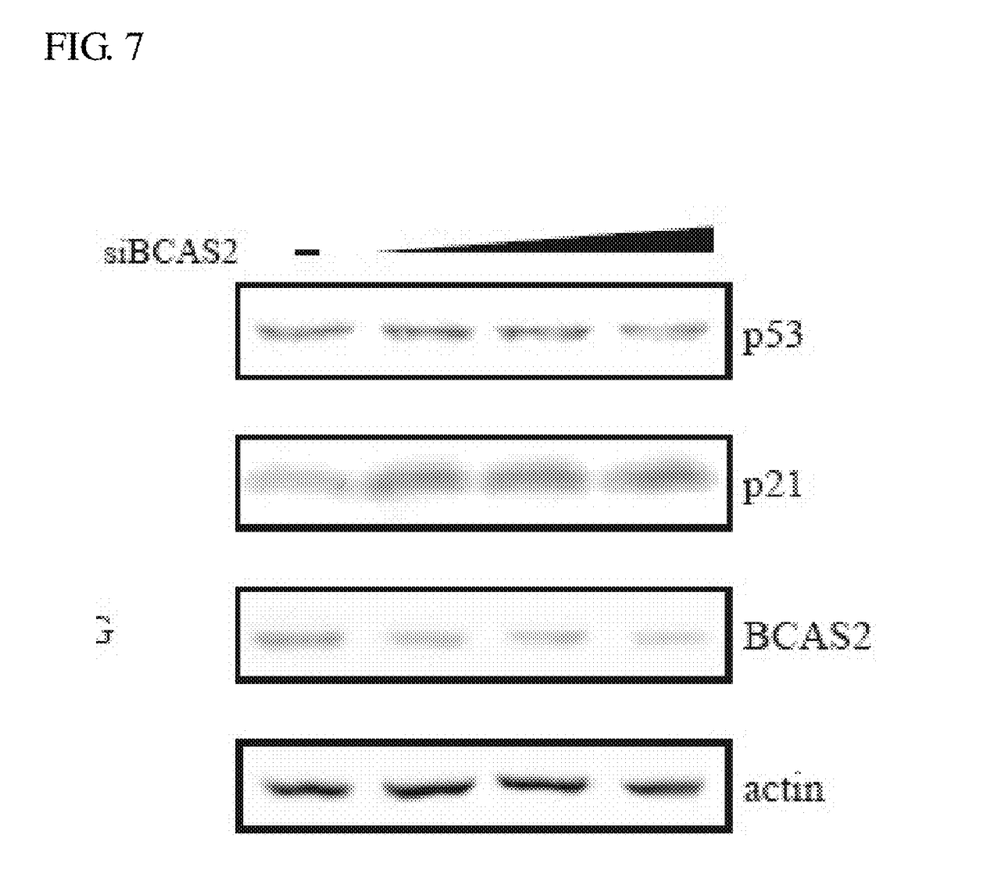
FIG. 7 shows the expression of p53, p21 and BCAS2 in MCF-7 cells transfected with various concentration of siBCAS2. The actin is used as internal control.

Furthermore, the effect of siBCAS2#434 showed a dose-dependent manner. BCAS2 protein expression decreased and p21 protein expression increased when the concentration of siBCAS2#434 increased in MCF-7 cell (FIG. 7).

Example 8

The Relationship between BCAS2, p53 and p21

Luciferase Activity Assays. Transient transfections were performed with FuGENE HD (Roche Applied Science) or electroporation according to the manufacturers' instructions. DNA constructs as indicated were transfected, including internal control (pRL-CMV). The total amount of plasmid transfected per dish was kept constant by adding empty pcDNA3 vector as needed. 24 h after each transfection, the medium was changed. After another 24 h, cells were harvested and the luciferase activity assayed by a Luminoskan Ascent luminometer (Thermo Labsystems).

Figure 8:
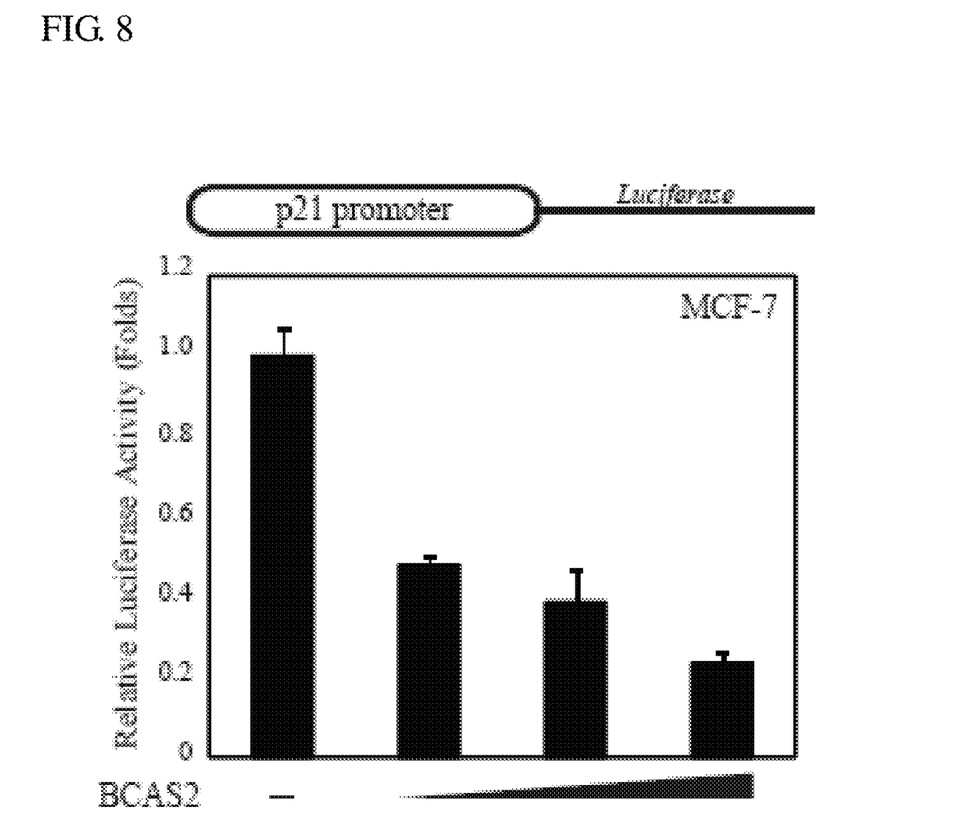
FIG. 8 shows relative p21 promoter driven luciferase activity of cells transfected with various concentration of siBCAS2.
Figure 9:
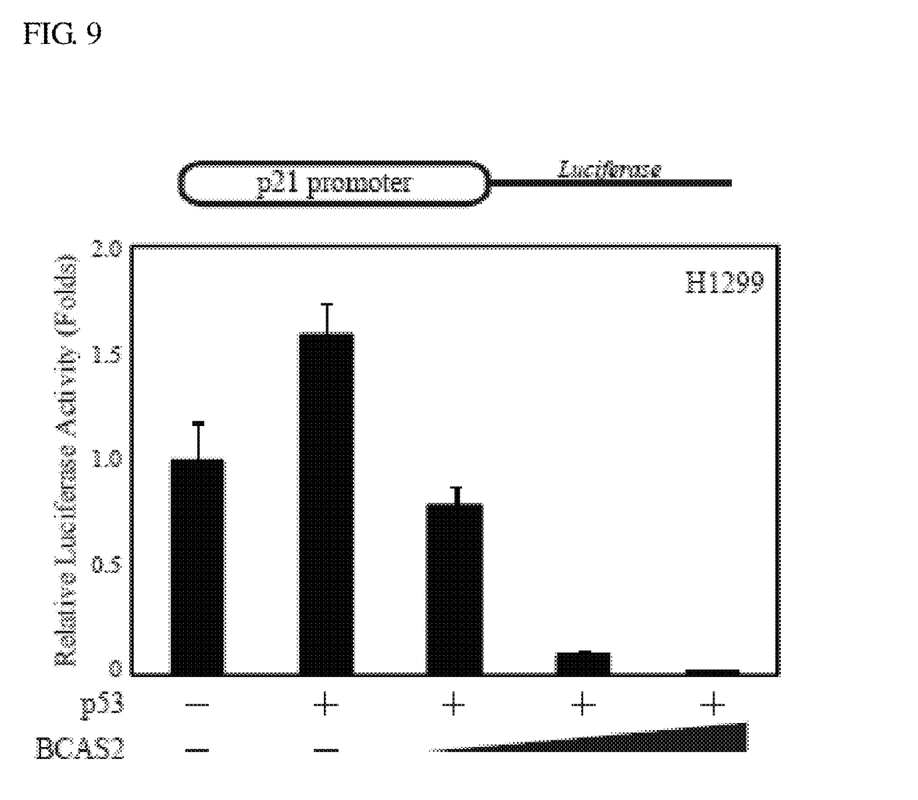
FIG. 9 shows relative p21 promoter driven luciferase activity of H1299 cells transfected with p53 and various concentration of BCAS2.

The result of the analysis showed that the increase of BCAS2 inhibited the activity of p21 promoter (FIG. 8). Furthermore, introduction of p53 into H1299 cell (p53 null) increased the activity of p21 promoter (FIG. 9 column 2). However, this effect of p53 was reduced with the introduction of BCAS2 with a dose-dependent manner (FIG. 9 columns 3-5).

Figure 10:
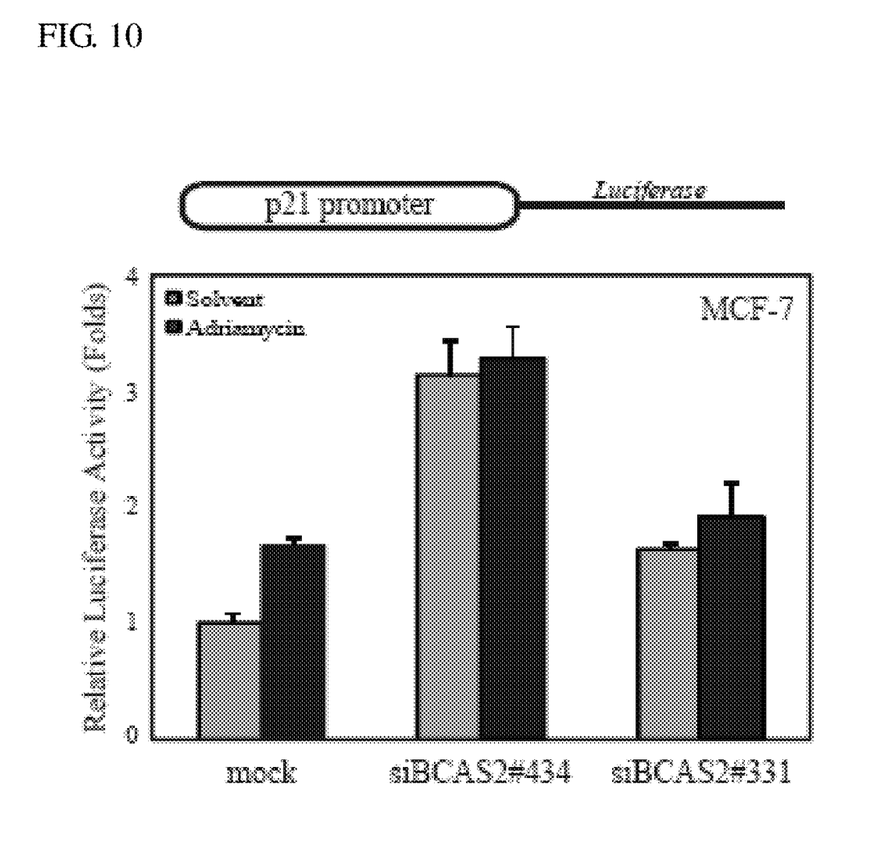
FIG. 10 shows relative p21 promoter driven luciferase activity of MCF-7 cells transfected with siBCAS2 with or without Adriamycin induction. Mock: electroporation without plasmid.

On the other hand, the p21 promoter activity was increased in MCF-7 cell transfected with siBCAS2#434. Induction of the intrinsic p53 expression by Adriamycin in this transfected MCF-7 cell did not cause further increase of p21 promoter activity (FIG. 10).

Example 9

The Effect of siBCAS2 on Cancer Cell Apoptosis

The RNAi clones of siBCAS2#331 and siBCAS2#434 were transfected into MCF-7 and H1299 cells. The transfected cell was then analyzed by Cell Cycle Analysis to estimate the apoptosis ratio. Collected cells from flask by trypsinization, and pooled the cells with the cells floating in the medium. Centrifuged the cell suspension and washed with medium twice. Counted cells and thoroughly resuspended $1\times10^6$ to $1\times10^7$ cells in 0.5 ml of PBS. Cells were fixed by 70% ethanol on ice for at least 2 hours. Centrifuged the ethanol-suspended cells, and decanted ethanol thoroughly. Wash with PBS and stain with propidium iodide at room temperature for 30 minutes. The cell fluorescence was measured by flow cytometry. The WinMDI software was used for data analysis.

Figure 11:
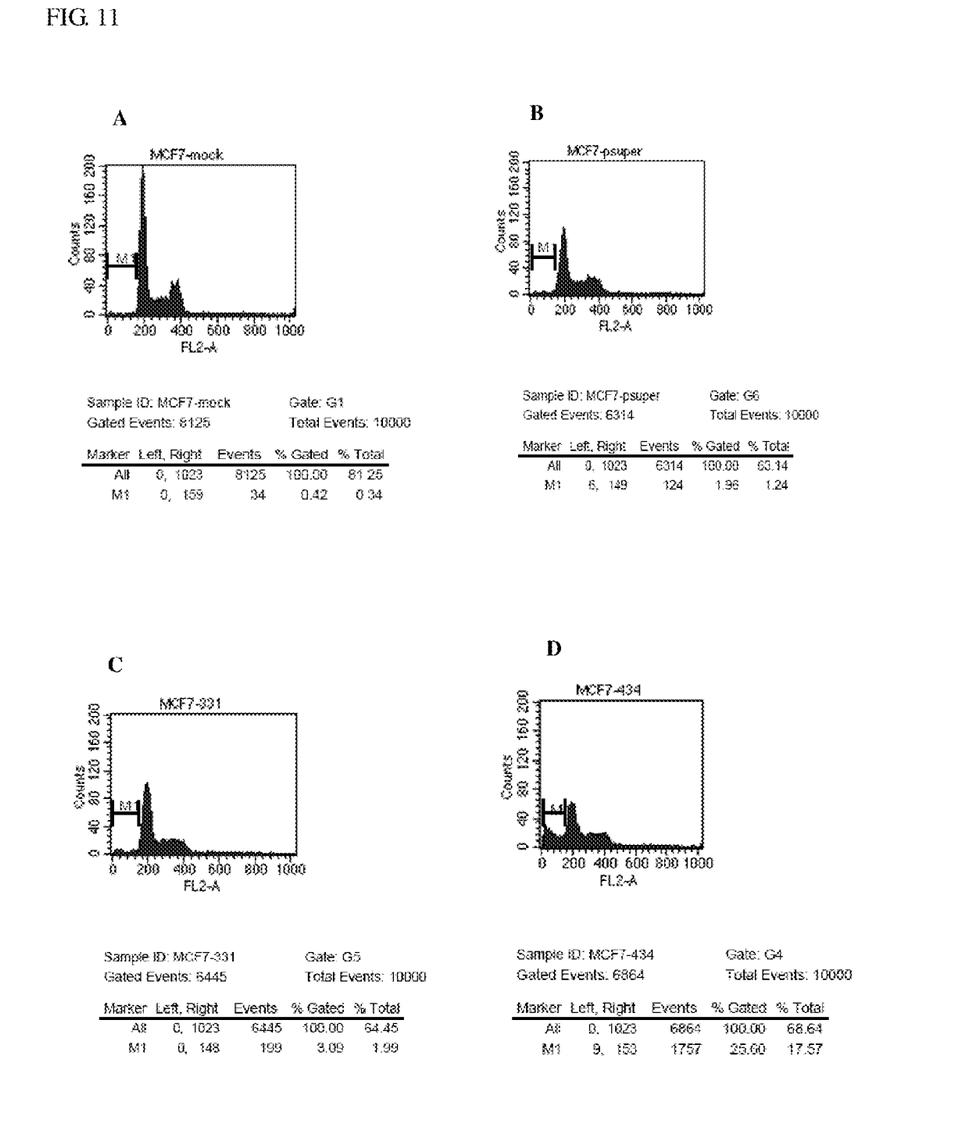
FIG. 11 shows apoptosis ratio of MCF-7 cells transfected with siBCAS2 measured by flow cytometry. (A) electroporated MCF-7 cells with no plasmid; (B) MCF-7 cells transfected with pSuper vector only; (C) MCF-7 cells transfected with siBCAS2#331; (D) MCF-7 cells transfected with siBCAS2 #434.
Figure 12:
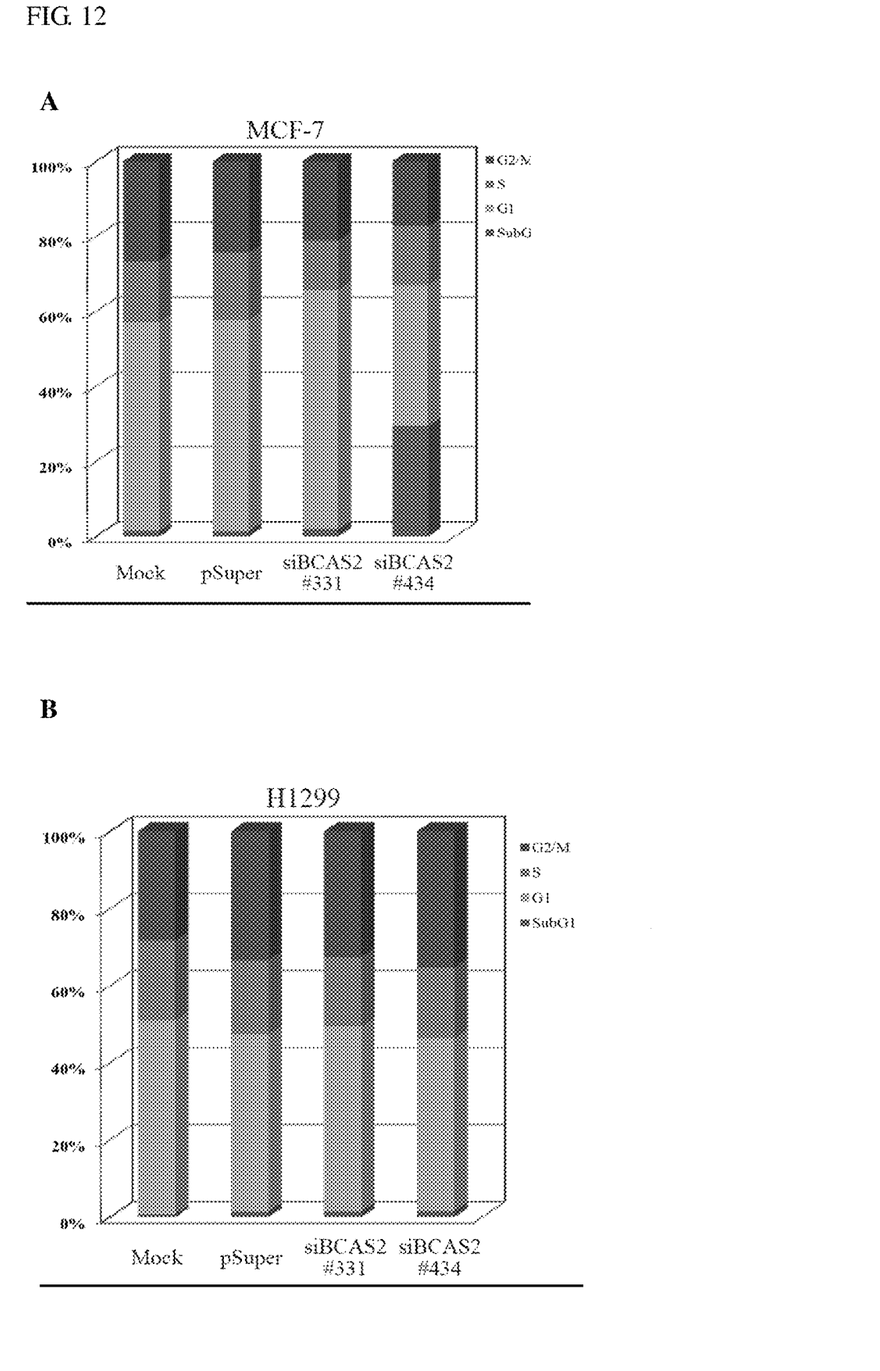
FIG. 12 shows apoptosis ratio of (A) MCF-7 cells and (B) H1299 cells.

The apoptosis percentage was 0.42 for MOCK (electroporation without plasmid), 1.96 for pSuper (vector only, control), 3.09 for siBCAS2#331, and 25.6 for siBCAS2#434 in MCF-7 cell (FIG. 11; FIG. 12A). FIG. 12B showed the apoptosis percentage of H1299 cell.

---

What is claimed is:

1. A nucleotide sequence of SEQ ID NO: 1.

2. A composition comprising a nucleotide sequence of small interfering RNA of BCAS2 gene, wherein the nucleotide sequence is SEQ ID NO: 1.

3. The composition of claim 2, wherein the nucleotide sequence is constructed in an RNAi vector.

4. The composition of claim 3, wherein the RNAi vector is pSuper.

5. A method for treating p53 containing cancer comprising administrating to a subject in need thereof an effective amount of the composition of claim 2.

6. The method of claim 5, wherein the cancer is breast cancer, prostate cancer or lung cancer.

7. The method of claim 6, wherein the cancer is breast cancer.

8. The method of claim 5, wherein the subject is a mammal.

9. The method of claim 8, wherein the subject is a human.

* * * * *